United States Patent [19]
Covington et al.

[11] 4,142,863
[45] Mar. 6, 1979

[54] ARTICLE CONTAINER FOR DISPENSING REAGENT SLIDES

[75] Inventors: Roger G. Covington; Stephen H. Miller, both of Rochester, N.Y.

[73] Assignee: Eastman Kodak Company, Rochester, N.Y.

[21] Appl. No.: 912,288

[22] Filed: Jun. 5, 1978

[51] Int. Cl.² .................... G01N 1/28; B65D 83/10
[52] U.S. Cl. ........................ 422/63; 221/226; 221/230; 221/279; 221/198; 422/57
[58] Field of Search ............ 23/259, 253 R; 221/279, 221/220, 226, 229, 230, 231, 238

[56] References Cited
U.S. PATENT DOCUMENTS

| | | | |
|---|---|---|---|
| 1,801,165 | 4/1931 | Macke | 221/238 |
| 3,533,744 | 10/1970 | Unger | 23/253 R |
| 3,767,083 | 10/1973 | Webb | 221/279 |
| 3,905,772 | 9/1975 | Hartnett et al. | 23/259 |

*Primary Examiner*—R.E. Serwin
*Attorney, Agent, or Firm*—M. S. Sales

[57] ABSTRACT

A container for dispensing reagent slides into apparatus which uses the slides to carry out quantitative chemical analysis of fluid samples. The container is formed of a plurality of casing parts which, when joined together, for a generally rectangular housing with a chamber for receiving a stack of the slides. The container fits into a complementary shaped nest in the analysis apparatus and has discontinuity means for inhibiting improper orientation of the container in the nest. A notch code on the container cooperates with structure on the nest to inhibit placing into the nest a container carrying reagent slides improper for the analysis test to be conducted.

10 Claims, 5 Drawing Figures

ARTICLE CONTAINER FOR DISPENSING REAGENT SLIDES

BACKGROUND OF THE INVENTION

1. Cross-Reference to Related Applications

Reference is made to commonly assigned, co-pending U.S. patent applications Ser. No. 751,912 entitled CHEMICAL ANALYZER, filed in the names of Louis C. Nosco, Anthony P. DiFulvio and Henry S. Adamski on Dec. 17, 1976, now abandoned; and Ser. No. 912,290 entitled ARTICLE DISPENSER APPARATUS, filed in the names of G. W. Scherer and R. G. Covington concurrently herewith.

2. Field of the Invention

The present invention relates to article containers from which individual articles can be sequentially removed from stacks of articles received in the containers.

3. Description of the Prior Art

In recent years, a number of automated systems have been developed for carrying out quantitative chemical analysis of fluid samples. While many of the commercially available systems utilize liquid reagents and require analyzer equipment having intricate solution handling and transport capabilities, one biological fluid analyzing apparatus in which discrete test slides containing individual dry reagents are metered through the apparatus to receive a drop of biological fluid to be tested is described in commonly assigned, co-pending U.S. patent application Ser. No. 751,912, entitled CHEMICAL ANALYZER filed on Dec. 17, 1976.

As described in that application, the test slides are stacked in containers, also called cartridges. A container may be received in a nest of the analyzing apparatus with a spring biased plunger arranged to enter the container through an opening. The plunger engages a movable element located in the container behind the slide stack to urge the slides forwardly toward a dispensing station at one end of the container. An example of such containers is disclosed in commonly assigned, copending U.S. patent application Ser. No. 912,290 entitled ARTICLE DISPENSER APPARATUS, filed in the names of G. W. Scherer and R. G. Covington concurrently herewith.

A push blade in the analyzing apparatus enters the container at the dispensing station to remove the leading slide from the container and move it into the analyzing apparatus by pushing it through a slot in the container wall. The remaining slides are sequentially moved forwardly in the container by the plunger as each preceding slide is removed.

The container has a substantially rectangular cross-sectional shape. As such, there is a distinct possibility that, in a busy hospital laboratory where numerous fluid samples are chemically analyzed daily, a container will occasionally be placed in its nest backwards. If unnoticed, such misorientation of the container may cause damage to the analyzer apparatus and would surely impose an unnecessary delay in the diagnosis process.

Each slide in a particular container has the same, appropriate reagent for a particular test, such as for example a reagent for testing glucose in blood serum. Other containers might house slides adapted for different tests. Unless the utmost care is exercised when a fresh cartridge is loaded into the analyzer nest, a container of slides with a reagent for one test may inadvertently be placed in the nest when slides for another test were in fact specified.

SUMMARY OF THE INVENTION

In accordance with the present invention, a container is provided with means to assure proper orientation of the container in the nest of an analyzer apparatus and with means to minimize the chance of introducing the wrong reagent to a chemical sample being tested. In a preferred embodiment of the invention, a container having a multi-part housing forming a chamber for a stack of articles, includes rib means adapted to interfere with the surfaces of the nest in all but one orientation of the container in the nest. The rib means inhibit improper insertion of the container into the nest unless the dispensing portion of the container is properly aligned in the apparatus. In order to minimize the possibility that the wrong container, and thereby the wrong reagent, will be loaded into the nest, a coding discontinuity may be provided at a predetermined position or positions on the exterior surface of the container. The number and positions of the discontinuities are determined in accordance with the reagent type, and the nest is provided with means to interfere with the insertion of all containers but those properly coded for the test intended to be run.

The invention, and its objects and advantages, will become more apparent in the detailed description of the preferred embodiment presented below.

DESCRIPTION OF THE PREFERRED EMBODIMENT

Figure 1:
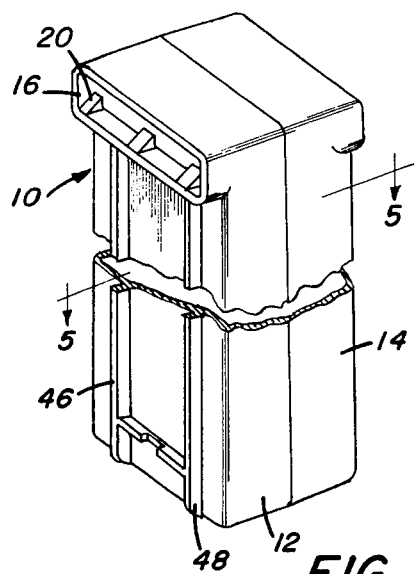
FIG. 1 is a perspective view of a slide container apparatus in accordance with a preferred embodiment of the present invention.
Figure 2:
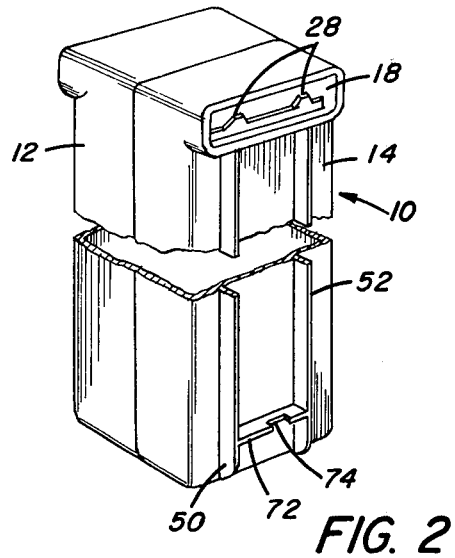
FIG. 2 is a perspective view of the apparatus of FIG. 1 taken from another angle.

In accordance with an illustrative embodiment of the present invention there is shown in FIGS. 1 and 2 a container, designated by the reference numeral 10, adapted to hold a stack of test slides for supply to a chemical analyzer as disclosed in aforementioned U.S. patent application Ser. No. 751,912. Container 10 includes a generally rectangular casing having two parts 12 and 14 shown separated in FIG. 3.

Figure 3:
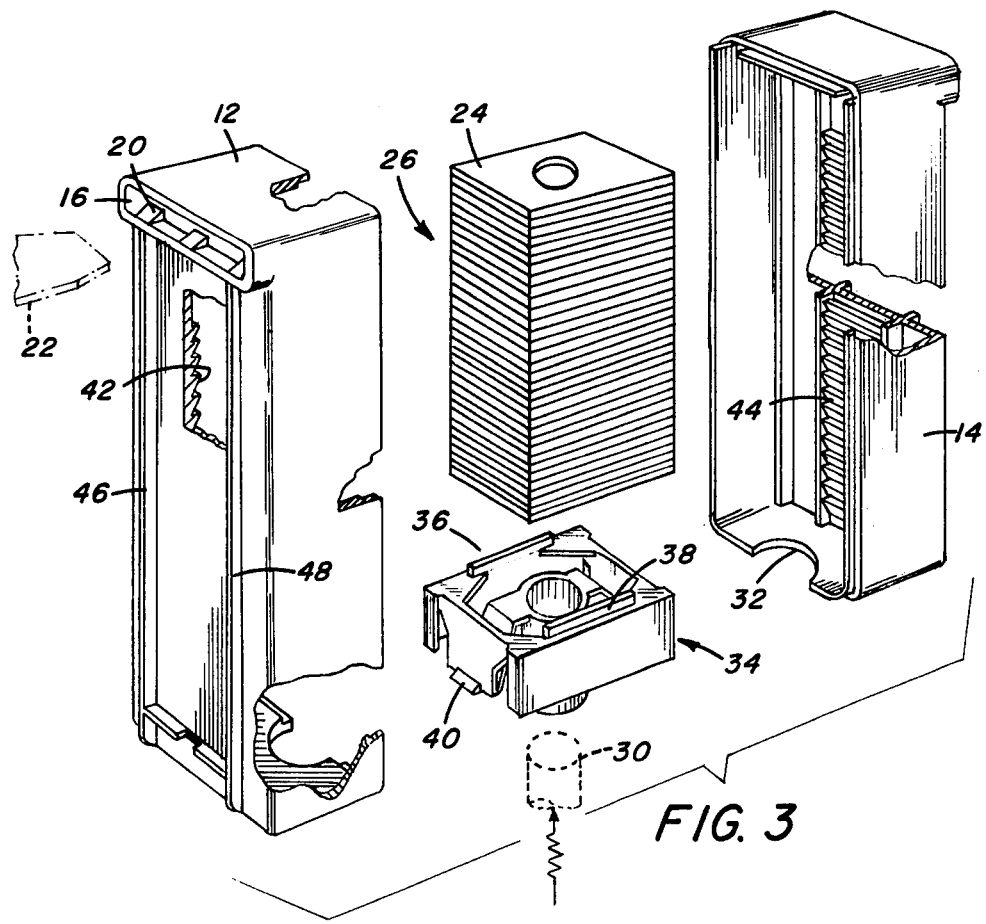
FIG. 3 is an exploded view of the apparatus of FIG. 1 showing a slide stack and a stack positioning element.

A dispensing station is provided at the forward end of container 10 (the top of the container as shown in FIGS. 1-3) and includes a pair of slots 16 and 18 for removing slides from the container. Slot 16 is ramped (three ramps 20 shown) to guide a push blade 22 (FIG. 3) of the analyzer into contact with the edge of the forward-most slide 24 of a slide stack 26. Slot 18 has a pair of tabs 28 which normally retain the slides in the container until pushed out by blade 22. The push blade extends through slot 16 to push the foremost slide out of slot 18 and into automatic slide handling means, not shown, of the analyzing apparatus.

When push blade 22 is withdrawn from slot 16, slide stack 26 is indexed forwardly (upwardly in the drawings) by a spring-loaded plunger 30 which extends through an opening 32 in the rear (or bottom) wall of the container to push against a stack positioning element 34. The stack positioning element is described in detail in aforementioned application Ser. No. 912,290 filed concurrently herewith. In general, the slide stack rests on a pair of rails 36 and 38 of the stack positioning element, which moves forwardly toward the dispensing station of container 10 as slides are removed from the container. A pair of anti-backup ratchet pawls 40 on either side of the stack positioning element engage successive teeth of ratchet teeth sets 42 and 44 respectively to inhibit movement of the slides rearwardly away from the dispensing station whenever the container is not in the analyzer nest. For example, should the container be taken from the analyzer nest after some but not all of the slides have been removed therefrom, plunger 30 would withdraw from opening 32 so that only the ratchet means keeps the slide stack from moving away from the dispensing station.

Figure 4:
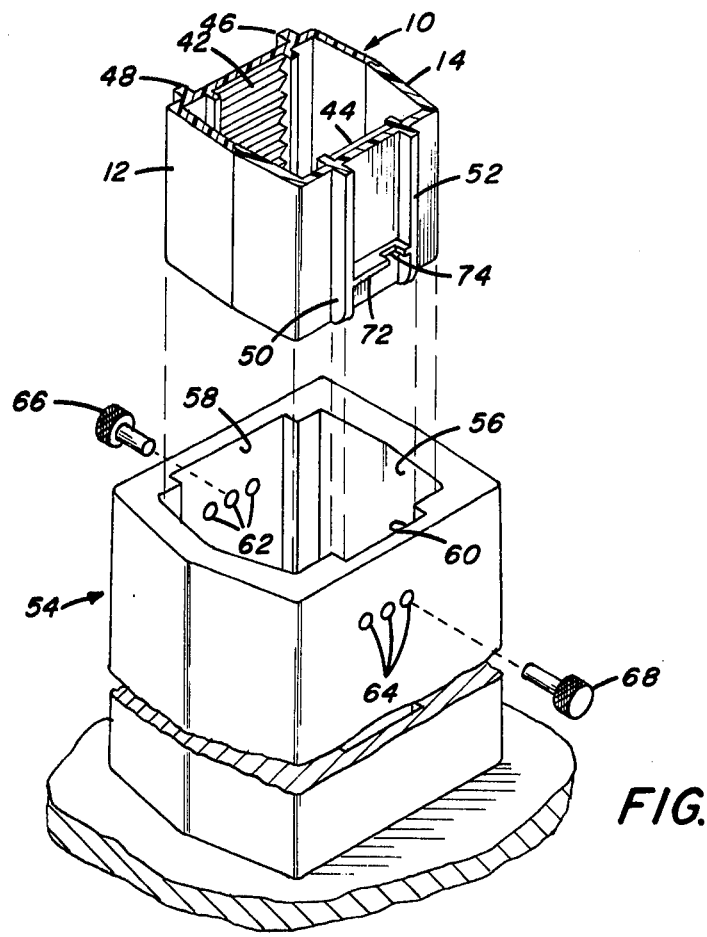
FIG. 4 is an exploded view of the apparatus of FIG. 1 and including a schematic illustration of a nest for the apparatus.
Figure 5:
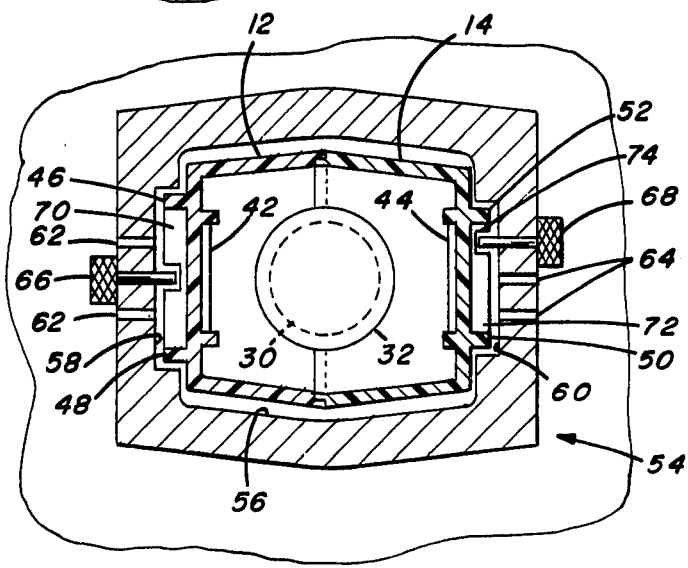
FIG. 5 is a cross-sectional view taken along line 5—5 in FIG. 1 including the nest shown in FIG. 4.

Referring to FIGS. 4 and 5, means are provided to insure proper orientation of container 10 in a nest 54 which is a part of the analyzer apparatus and is adapted to receive the container. As discussed hereinbefore, it is important that the container not be placed in nest 54 improperly.

Casing part 12 has a parallel pair of vertical rails 46 and 48, and casing part 14 has a similar pair of rails 50 and 52, the latter rail pair being more closely spaced than the former rail pair. As can be seen in FIG. 5, nest 54 has a chamber 56 shaped to conform to the cross sectional shape of container 10. A pair of channels 58 and 60, best seen in FIG. 4, on opposite interior walls of chamber 56 are arranged to receive rail pairs 46 and 48 and rails 50 and 52, respectively. Channel 58 is wider than channel 60 because rails 46 and 48 are wider spaced than rails 50 and 52.

Should an attempt be made to insert a container 50 backwards into chamber 56 of the nest, rail pair 46 and 48 would be aligned with recess 60 and rail pair 50 and 52 would be aligned with recess 58. Since recess 60 is not as wide as the spacing of rails 46 and 48, the container will not fit into chamber 56. Thus, improper orientation of containers in nest 54 is prevented.

As mentioned hereinbefore, each slide in a particular container has the same, appropriate reagent for a particular biological fluid analysis. Other containers might house slides adapted for different tests. In setting up the analyzer apparatus to run one or a series of tests of a particular kind, it is anticipated that an operator will select a container loaded with the proper slides and place that container in nest 54. Another feature of the present invention, is the provision of means on the container which cooperates with means on the nest to inhibit placement into the analyzer apparatus of a container of improper slides for the test to be conducted.

Referring to FIGS. 4 and 5, a series of holes 62 and 64 are provided in the walls of nest 54 in the regions of channels 58 and 60, respectively. The holes are adapted to selectively receive pins 66 and 68 which, when inserted into the holes, extend into the nest channels. Each biological test to be performed may be assigned a unique combination of pin arrangement in holes 62 and 64.

On the container, a web 70 extends between rails 46 and 48, and a web 72 extends between rails 50 and 52. A portion of each web may be removed in a selected area of the web, such as by a punching operation, to form a notch 74. The position of the notch along the web is predetermined in accordance with the particular chemical reagent carried by the slides in the container.

In preparing the apparatus to perform a specific biological test, the operator first moves pins 66 and 64 into the proper ones of holes 62 and 64 for that particular test. The operator would thereupon select a container 10 having slides suitable for that test, and insert the container into nest 54.

If the operator has properly positioned pins 66 and 68 and has selected the correct container, the pins will be aligned with the notches in webs 70 and 72, and the container will be received in the nest. However, should the operator error in either the placement of the pins or in the selection of the container, the web notches will not align with the pins, and the container will not seat in the nest. This will immediately be noticeable by the operator, and he will be able to correct his error. Of course, it is possible that a double error may occur wherein the operator places the pins in the wrong holes and then selects the wrong container which matches the incorrect pin placement. However, the probability of such a double error is very small.

The invention has been described in detail with particular reference to a preferred embodiment thereof, but it will be understood that variations and modifications can be effected within the spirit and scope of the invention.

What is claimed is:

1. A container for dispensing reagent slides into apparatus (1) having a nest into which said containers are insertable and (2) adapted to use reagent slides to carry out quantitative chemical analysis of fluid samples; said container comprising:
   a plurality of separate casing parts adapted to be joined together to form a generally rectangular housing having (1) a dispensing station for dispensing slides to the apparatus when the container is properly oriented in the nest and (2) a chamber for receiving a stack of the slides to be dispensed into the apparatus through said dispensing station; and
   discontinuity means, on at least one of said casing parts, for inhibiting insertion of said container into the nest in all orientations other than the proper orientation, whereby said dispensing station is aligned for injecting slides into the apparatus.

2. A container as set forth in claim 1 wherein said discontinuity means includes a projection on the container positioned to interfere with surfaces of the nest in orientations other than said proper orientation.

3. A container as set forth in claim 1 wherein the nest includes surfaces defining a pair of slots of different dimensions and said discontinuity means comprises:
   a first pair of ribs spaced apart by a distance substantially equal to the dimension of one of the slots; and
   a second pair of ribs spaced apart by a distance substantially equal to the dimension of the other of the slots.

4. A container as set forth in claim 3 wherein said ribs of said first and second rib pairs are parallel.

5. A container as set forth in claim 3 wherein:
   said container is adapted to be inserted into the nest in a predetermined direction; and
   said first and second rib pairs extend along the container in a direction parallel to the direction of insertion of said container into the nest.

6. A container as set forth in claim 1 wherein the nest includes surfaces defining a pair of slots of different dimensions and said discontinuity means comprises:

a first pair of ribs on one of said casing parts and spaced apart by a distance substantially equal to the dimension of one of the slots; and a second pair of ribs on the other of said casing parts and spaced apart by a distance substantially equal to the dimension of the other of the slots.

7. A container for dispensing reagent slides into apparatus (1) having a slotted nest into which said containers are insertable and (2) adapted to use reagent slides to carry out quantitative chemical analysis of fluid samples; said container comprising:

a plurality of separate casing parts adapted to be joined together to form a generally rectangular housing having (1) a dispensing station for dispensing slides to the apparatus when the container is properly oriented in the nest and (2) a chamber for receiving a stack of the slides to be dispensed into the apparatus through said dispensing station;

a pair of ribs spaced apart by a distance substantially equal to the dimension of the nest slot for inhibiting insertion of said container into the nest in all orientations other than the proper orientation, whereby said dispensing station is aligned for injecting slides into the apparatus; and a web, extending between said ribs, and adapted to receive a code discontinuity indicative of particular chemical analysis to be performed by the reagent slides received in said chamber.

8. A container as defined in claim 7 wherein said web has a code discontinuity at one of a plurality of positions indicative of particular chemical analysis to be performed by the reagent slides received in said chamber.

9. A container for dispensing reagent slides into apparatus (1) having a nest into which said containers are insertable and (2) adapted to use reagent slides to carry out quantitative chemical analysis of fluid samples; said container comprising:

a plurality of separate casing parts adapted to be joined together to form a generally rectangular housing having (1) a dispensing station for dispensing slides to the apparatus when the container is properly oriented in the nest and (2) a chamber for receiving a stack of the slides to be dispensed into the apparatus through said dispensing station;

discontinuity means, on at least one of said casing parts, for inhibiting insertion of said container into the nest in all orientations other than the proper orientation, whereby said dispensing station is aligned for injecting slides into the apparatus; and means for receiving a code discontinuity indicative of particular chemical analysis to be performed by the reagent slides received in said chamber.

10. A container for dispensing reagent slides into apparatus (1) having a nest into which said containers are insertable and (2) adapted to use reagent slides to carry out quantitative chemical analysis of fluid samples; said container comprising:

a plurality of separate casing parts adapted to be joined together to form a generally rectangular housing having (1) a dispensing station for dispensing slides to the apparatus when the container is properly oriented in the nest and (2) a chamber for receiving a stack of the slides to be dispensed into the apparatus through said dispensing station; and means for receiving a code discontinuity indicative of particular chemical analysis to be performed by the reagent slides received in said chamber.

* * * * *